United States Patent [19]

Montagnon

[11] 4,066,511
[45] Jan. 3, 1978

[54] ANALYTIC DEVICE AND METHOD

[76] Inventor: Paul A. F. Montagnon, La Balme-les-Grottes Isere, France

[21] Appl. No.: 603,383

[22] Filed: Aug. 11, 1975

[30] Foreign Application Priority Data

Aug. 12, 1974 France .............................. 74.28639

[51] Int. Cl.$^2$ .............................................. C12K 1/04
[52] U.S. Cl. ............................. 195/103.5 M; 195/127;
23/253 TP
[58] Field of Search ................ 195/103.5 R, 127, 139,
195/103.5 M; 23/253 TP

[56] References Cited

U.S. PATENT DOCUMENTS

| 3,249,513 | 5/1966 | Babson | 195/103.5 R |
|---|---|---|---|
| 3,455,656 | 7/1969 | Roberts et al. | 23/253 TP |
| 3,616,258 | 10/1971 | Kronish et al. | 195/103.5 R |
| 3,802,842 | 4/1974 | Lange et al. | 195/103.5 R |

OTHER PUBLICATIONS

Bergey's Manual of Determinative Bacteriology, Breed, Murray and Smith; Seventh Edition p. 626, William and Wilkinson; 1957.

*Primary Examiner*—Lionel M. Shapiro
*Assistant Examiner*—Robert J. Warden

*Attorney, Agent, or Firm*—Kenyon & Kenyon, Reilly, Carr & Chapin

[57] ABSTRACT

The present invention provides an apparatus useful for the detection of an unknown microorganism such as a bacterium in a liquid nutritive medium comprising a tube adapted to receive a portion of a nutritive liquid medium containing an unknown bacterium and means for sealing off said tube and a test strip comprising at least one liquid reactive surface capable of being immersed in said liquid medium, said surface containing nutritive elements complementary to the nutritive elements in the liquid medium and a reagent which reacts with said bacterium, said reagent being incapable of inhibiting growth of said specimen and being non-toxic to said specimen, and at least one vapor-reactive surface incapable of being immersed in the liquid medium when said reactive surface is immersed in the liquid medium, said surface containing reagents which are toxic to said bacterium and react on contact with vapors emitted by the liquid medium due to the presence of the bacterium contained thereon.

The invention also provides a novel method for detecting a bacterium, a test strip and a flexible cover for glass containers.

3 Claims, 4 Drawing Figures

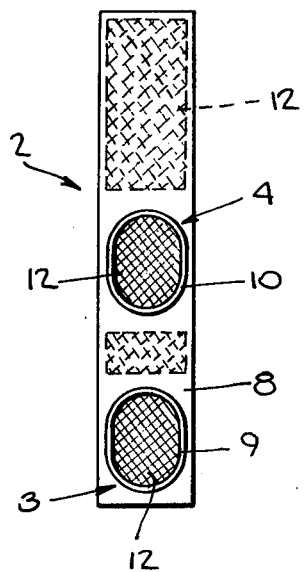
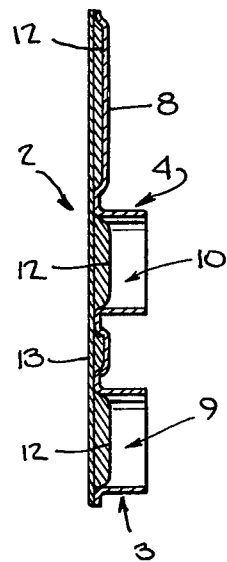
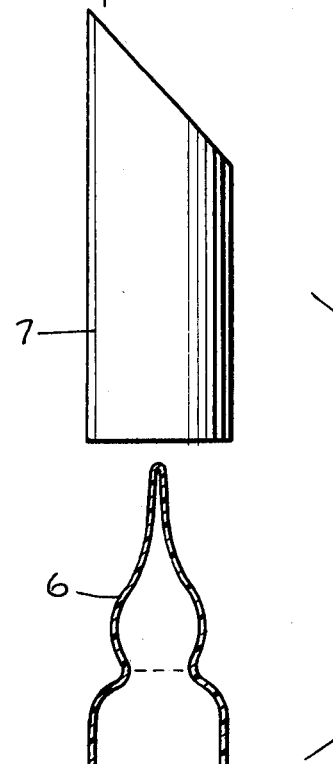
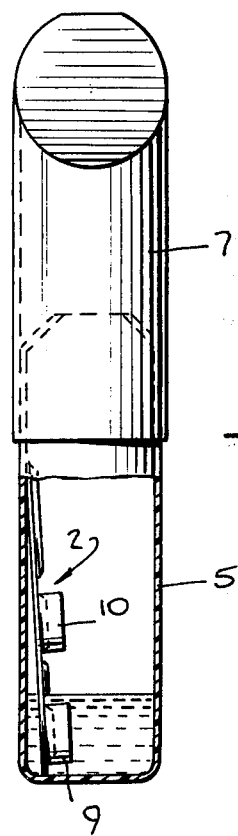

ANALYTIC DEVICE AND METHOD

BACKGROUND OF THE INVENTION

The present invention is concerned with an analytical device and more particularly with a method for the rapid detection of microorganisms from an isolating medium, that is to say the enabling of a diagnosis by a process of elimination in the case of a search for a particular microbe.

It is known in the art that reactions of bacteria in a liquid nutritive medium can take place in test tubes, with the liquid medium necessary for the growth of bacteria having been freshly prepared just prior to the reaction. Furthermore, certain reactions, such as bacterial reactions in a urea-indole medium, denature the reaction medium, which eliminates the possibility of conductiong other reactions in the same medium at a later time. These reactions, have the further disadvantage of occurring very slowly. The reading of a reaction in a urea-indole medium for example is only possible after about four hours. Other reactions are achieved by immersing reactive test strips in the test tubes. This procedure presents the inconvenience because it necessitates a dense medium and equally because it denatures the reaction medium, which as mentioned above prevents the medium from being utilized further.

The present invention substantially alleviates the aforementioned problems by providing an analytical device including a test strip which enables the obtaining of rapid results and enables the bacteria being tested to effect the ultimate reactions in liquid media. The present invention is also concerned with a process for determining a microorganism such as a bacterium and a novel cover for glass ampules.

SUMMARY OF THE INVENTION

In one embodiment of this invention an analytical device is provided which comprise in combination:
a. a tube adapted to receive a portion of a nutritive liquid medium containing an unknown bacterium and having means for sealing-off said tube; and
b. a test strip comprising:
1. at least one liquid-reactive surface intended to be immersed in said liquid medium; said surface containing in a dry state some nutritive elements complementary to the nutritive elements in the liquid medium and a reagent which reacts with said bacterium, said reagent being incapable of inhibiting growth of said bacterium and being non-toxic to said bacterium; and
2. at least one vapor-reactive surface not intended to be immersed in the liquid medium when said liquid-reactive surface is immersed in the liquid medium, said surface containing in a dry state a reagent which may be toxic to said specimen and reacts on contact with vapors or gases emitted by the liquid medium due to the presence of the bacterium therein.

Thus the analytical device is the combination of a tube which has means for obturation or sealing off of the tube and contains at least a portion of a nutritive liquid medium permitting the growth of an unknown microorganism such as a bacterium, and a test strip which has at least two reactive regions, one of which is situated in close proximity to the end of the strip, and is intended to be immersed in the liquid contained in the tube and contains, in its dry state, some nutritive elements complementary to the liquid medium enclosed in the tube and at least one reagent which permits spontaneous reactions with the bacterium in the liquid medium. The reagent must be non-toxic to the bacterium and not capable of inhibiting their growth. The strip also contains at least one other surface situated on the strip which is not to be immersed in the liquid medium and contains, in its dry state, a reagent or reagents which are toxic to the bacterium and react on contact with vapors emitted by the liquid medium in the presence of the bacterium.

The reactions take place in a tube placed in an incubator at about 37° C. According to the nature of the bacteria present, a reaction in the liquid stage can occur and is visually indicated by a change of color. Furthermore, the liquid medium releases some volatile products which can initiate some reactions with the toxic reagents contained in a dry state in the areas of the strips not immersed. These reactions are also indicated visually by changes in color of these reactive regions. It is of interest to note that such reactions do not completely denature the liquid medium contained in the tube thus permitting new reactions to be conducted using the same medium at a later time.

The analytical device is used to detect the presence of bacteria and as a screen for preliminary identifying a class or classes of bacteria. If the screen gives positive results, that is a visual change in color corresponding to a positive reaction between the test strip and the bacteria, the investigation can be extended to a more elaborate testing procedure for a more accurate determination of the bacteria as, for example, by using the twenty-test or fifty-test strip method as outlined in U.S. application Ser. No. 453,434, filed Mar. 21, 1974.

Another advantage of this device is that it can be stored for a relatively long period of time. Furthermore, the tube can contain chemical products in a liquid form which cannot be dehydrated or decomposed while the active surfaces of the strip contain chemical products complementary to those of the liquid medium, preserved perfectly when dry but poorly or not at all when in the liquid medium.

Other advantages include the rapid rate of analysis, on the order of two hours, and the easy preparation of the components for use.

Advantageously the tube contains, in addition to a portion of a nutritive liquid medium permitting the growth of bacteria, at least one reactive product which enables spontaneous reactions with the bacteria to occur in the liquid medium and yet is non-toxic with respect to these bacteria and does not inhibit their growth.

The test stip of the invention comprises a primary sheet of material such as a plastic material having a plurality of openings equal to the number of surfaces, a weave of the same material placed over the openings and a sheet of flat covering material, the woven material being arranged between the two aforementioned sheets and the three parts sealed together by a heat-sealing process.

The reagents are deposited on the weave of material adjacent to the openings as a solution which is allowed to evaporate to remove solvent therefrom and to leave the surface impregnated with the reagents.

In still another embodiment of this invention, a flexible cap for a glass container having a narrow sealed neck such as a heat-sealed ampulle or vial is provided which performs the dual function of (a) permitting opening of the container by breaking of the narrow sealed neck through pressure exerted on the flexible cap in the vicinity of the narrow neck and (b) enclosing the opened container to protect and seal the contents thereof.

The invention will be more completely described with reference to the following drawings and description.

BRIEF DESCRIPTION OF THE DRAWINGS

FIG. 1 is a front view of the test strip.
FIG. 2 is a side view of the test strip.
FIG. 3 is a view of the tube before utilization.
FIG. 4 is a view of the tube and the test strip in the course of testing.

DETAILED DESCRIPTION OF THE PREFERRED EMBODIMENTS

Referring to FIGS. 1 and 2, the test strip 2 contains at least two reactive surfaces 3 and 4. The reactive surface 3 contains in its dry state some nutritive elements and some products which allow spontaneous reactions with the bacteria in the liquid medium, these products being non-toxic for the bacteria and not inhibiting their growth. The reactive surface 4 contains products in a dry state which upon reacting when in contact with gases emitted by the liquid medium in the presence of certain bacteria are toxic.

FIG. 3 shows a tube 5 which before utilization is sealed. The upper part of the tube 6 may be cut off to permit the introduction of reagents, the cap 7 having been designed to seal this tube after introduction of reagents. Tube 5 can contain 1 ml of culture medium and some agents complementary to the agents contained on the reactive region 3 which region can be immersed in the culture medium. The cover is made of a flexible material such as a resin plastic material and fits slidably over the upper part of the tube 6. The cover also serves to break the upper part of the tube before use by pressing the angled portion of the cover against the upper portion of the tube using, for example, "thumb pressure." In this manner the tube can be opened safely without directly touching the glass with the hand. The broken portion of the tube is then removed, the test strip 2 is placed in the tube and the tube is resealed with the cover 7.

The strip 2 consists of a primary sheet of material 8 having two perforations 9 and 10 corresponding to the reactive regions 3 and 4, respectively, a woven or textured tissue or mesh 12 placed over the preforations 9 and 10 and the top portion of the strip so that the upper end portion of the strip serves as a gripping area for the test strip, and a flat cover sheet 13 of plastic material covering the primary sheet with the woven material over the preforations being exposed between sheets 8 and 13. The sheets can be made of plastic materials such as polyvinyl chloride, polyamide or other synthetic polymer. The three parts are assembed by joining or welding at high frequency in the case of polyvinyl chloride or by a heat process, by impulses, or by ultrasonic vibrations, for the case where the materials are made from polyamides or other polymers.

In practice, the upper portion 6 of the tube 5 is broken off, then a suspension of the specimen to be analyzed is made. Then the strip 2 is introduced into tube 5 so that only region 3 is immersed, region 4 being located just above the liquid. The tube is covered by cap 7 and placed in an incubator at 37° C for 2 hours.

The result of the reactions is indicated by eventual changes in the color of the liquid and/or the reactive regions. Thus, for example, the culture medium can include as a reagent "ONPG" (-galactosidose) which turns yellow for a positive reaction, while the region 3 may contain "TDA" (tryptophane) which turns maroon on reaction, and region 4 may contain "IND" or "INDOLE" (Kovacs reagent) which turns to violet on reaction.

The test strip 5 can contain a plurality of operational or reactive regions 3 and a plurality of operational or reactive regions 4 in accordance with the invention.

What is claimed is:

1. An analytical testing kit adapted to detect the presence of at least one of a plurality of different predetermined microorganisms in a test specimen comprising:
    a. a tubular receptacle having a portion therein containing a liquid medium having both nutrients for enabling the growth of microorganisms of the specimen when disposed therein and a first predetermined reagent which can react with a predetermined microorganism of the plurality to give an indication, the tubular receptacle additionally having means for sealing the liquid medium within the tube; and
    b. an elongated test strip adapted to be inserted into the tubular receptacle when the sealing means is removed, the test strip having
        1. at least one liquid-reactive region adjacent one end portion of the strip adapted to be immersed in the liquid medium, the liquid-reactive region containing other nutrients complementary to the nutrients of the liquid medium and a second predetermined reagent which can react to give an indication when another predetermined microorganism of the plurality is cultured in the liquid medium, the second predetermined reagent being incapable of inhibiting the growth of the plurality of different microorganism and being non-toxic to the plurality of microorganisms; and
        2. at least one vapor-reactive region, the vapor-reactive region being adapted to be disposed out of the liquid medium when the liquid-reactive region is immersed in the liquid medium, said vapor-reactive region containing a third predetermined reagent which can react to give an indication when contacted with a predetermined vapor emitted from the liquid medium in response to the presence of a predetermined microorganism of the plurality of microorganisms.

2. An analytical testing strip for detecting the presence of at least one of a plurality of different microorganisms in a test specimen, the testing strip being elongated and adapted to be inserted into a tubular receptacle having a portion therein containing a liquid medium having both nutrients for enabling the growth of microorganisms of the specimen when disposed therein and a first predetermined reagent which can react with a predetermined microorganism of the plurality to give an indication, the tubular receptacle additionally having means for sealing the liquid medium within the tube, the testing strip comprising:
    a. at least one liquid-reactive region adjacent one end portion of the strip adapted to be immersed in the liquid medium, the liquid-reactive region containing other nutrients complementary to the nutrients of the liquid medium and a second predetermined reagent which can react to give an indication when another predetermined microorganism of the plurality is cultured in the liquid medium, the second predetermined reagent being incapable of inhibiting the growth of the plurality of different microorganism and being non-toxic to the plurality of microorganisms; and b. at least one vapor-reactive region, the vapor-reactive region being adapted to be disposed out of the liquid medium when the liquid-reactive region is immersed in the liquid medium, said vapor-reactive region containing a third predetermined reagent which can react to give an indication when contacted with a predetermined vapor emitted from the liquid medium in response to the presence of a predetermined microorganism of the plurality of microorganisms.

3. A process for detecting the presence of at least one of a plurality of different predetermined microorganisms in a test specimen by use of a tubular receptacle having a portion therein containing a liquid medium having both nutrients for enabling the growth of microorganisms of the specimen when disposed therein and a first predetermined reagent which can react with a predetermined microorganism of the plurality to give an indication, the tubular receptacle additionally having means for sealing the liquid medium within the tube, and an elongated test strip adapted to be inserted into the tubular receptacle when the sealing means is removed, the test strip having at least one liquid-reactive region adjacent one end portion of the strip adapted to be immersed in the liquid medium, the liquid-reactive region containing other nutrients complementary to the nutrients of the liquid medium and a second predetermined reagent which can react to give an indication when another predetermined microorganism of the plurality is cultured in the liquid medium, the second predetermined reagent being incapable of inhibiting the growth of the plurality of different microorganism and being non-toxic to the plurality of microorganisms, and at least one vapor-reactive region, the vapor-reactive region being adapted to be disposed out of the liquid medium when the liquid-reactive region is immersed in the liquid medium, said vapor-reactive region containing a third predetermined reagent which can react to give an indication when contacted with a predetermined vapor emitted from the liquid medium in response to the presence of a predetermined microorganism of the plurality of microorganisms, the process comprising the steps of:

a. placing the test specimen into the liquid medium in the tubular receptacle, the nutrient in the liquid medium enabling the test specimen to be cultured, b. placing the elongated test strip into the tubular receptacle when the sealing means is removed with the liquid-reactive region of the test strip immersed in the liquid medium and the vapor-reactive region disposed out of the liquid medium, c. permitting the test specimen to be cultured, to react with any one of the first and second reagents, and any vapor from the liquid medium to react with the third reagent, d. sensing the liquid medium for a possible indication by the first reagent, e. further sensing the liquid-reactive portion of the test strip for possible indication by the second reagent, f. additionally sensing the vapor-reactive region of the test strip for possible indication by the third reagent, and g. compiling the results of the steps of (c), (d), and (e) for determining the presence of at least one of a plurality of different predetermined microorganisms.

* * * * *